United States Patent [19]

Jarry et al.

[11] Patent Number: 5,686,477

[45] Date of Patent: Nov. 11, 1997

[54] 5-(ARLOXYMETHYL)OXAZOLINES

[75] Inventors: Christian Jarry, Artigues-Pres-Bordeaux; Isabelle Forfar, Bordeaux; Jean-Jacques Bosc, Pompignac; Pierre Renard, Versailles; Elizabeth Scalbert, Boulgone; Béatrice Guardiola, Saint Cloud, all of France

[73] Assignee: Adir et Compagnie, Courbevoie, France

[21] Appl. No.: 556,797

[22] Filed: Nov. 2, 1995

[30] Foreign Application Priority Data

Nov. 3, 1994 [FR] France ................. 94 13087

[51] Int. Cl.[6] ............. C07D 263/00; C07D 263/06; A01N 43/76
[52] U.S. Cl. ............................. 514/377; 548/233
[58] Field of Search .......................... 548/233; 514/377

[56] References Cited

U.S. PATENT DOCUMENTS

| | | | |
|---|---|---|---|
| 3,052,688 | 9/1962 | Wolf | 548/233 |
| 3,110,650 | 11/1963 | Fischer et al. | 514/282 |
| 3,161,650 | 12/1964 | Poos | 460/18 |
| 3,278,382 | 10/1966 | Poos | 514/377 |
| 3,577,428 | 5/1971 | Suh | 548/233 |
| 3,626,067 | 12/1971 | Harvey, Jr. | 514/377 |
| 3,637,726 | 1/1972 | Faith et al. | 548/233 |
| 3,818,028 | 6/1974 | Faith | 548/233 |
| 5,081,137 | 1/1992 | Descas et al. | 514/377 |
| 5,153,210 | 10/1992 | Ainsworth et al. | 514/369 |

OTHER PUBLICATIONS

Jarry et al. "Synthese et Etude Structural D'amino–2 Oxazolines–2 A Action Antihypertensive", Bulletin de la Societe de Pharmacie de Bordeaux, pp. 153–162, 1981.

Misiaszec et al. "5–Substituted–3–Pheracyl–2–Iminoaxazolidines as Anti––Arrhythmic and Local Anaesthetic Agents", Eur. J. Med. Chem., 25, pp. 375–382, 1990.

Abdallah, "Effect of APMO* on Pulmonary and Arterial Blood Pressure . . . ", European Journal of Pharmacology, 27, pp. 249–251, 1974.

Abdallah, "The Cardiovascular Activity of . . . APMO", Toxicology and Applied Pharmacology, 26, 513–522 (1973).

Jarry et al., Heterocycles, 36, pp. 2465–2473, 1993.

Jarry et al., Acta Cryst., B38, pp. 964–966, 1982.

Misiazek et al., C.R. Acad. Sci. Paris, t.307, Series II, pp. 1189–1193, 1988.

Farfar et al., "2–Amino–2–oxazolines, III . . . ", Archiv. Der Pharmazie und Berichte Der Deutschen Pharmazeutischen Gesellschaft, 323, pp. 905–909, 1990.

Primary Examiner—Jeffrey C. Mullis
Attorney, Agent, or Firm—The Firm of Gordon W. Hueschen

[57] ABSTRACT

The invention relates to compounds of formula (I):

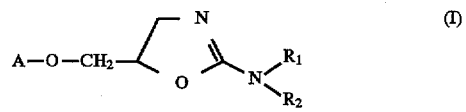

wherein:

$R_1$ and $R_2$ are selected, each independently of the other, from hydrogen and an alkyl radical, A is selected from the radicals:

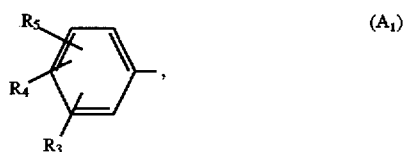

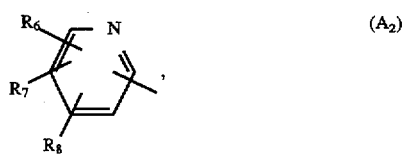

and

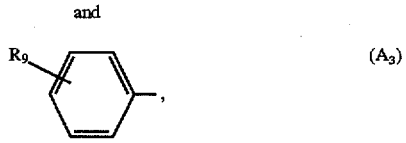

wherein:

$R_3$ represents a radical selected from halogen, alkyl, alkoxy, amino, 2-acetyl, alkylamino, dialkylamino, carboxy, alkoxycarbonyl, trifluoromethyl and cyano, $R_4$, $R_5$, $R_6$, $R_7$ and $R_8$ are selected, each independently of the others, from hydrogen, a halogen, an alkyl, alkoxy, amino, alkylamino, dialkylamino, carboxy, alkoxycarbonyl, cyano and a trifluoromethyl radical, $R_9$ represents the nitro radical, with the proviso that A cannot represent a grouping selected from: dihalophenyl, trihalophenyl, 4-methylphenyl, 4-chlorophenyl, 4-methoxyphenyl, 4-tert-butylphenyl and 3-(dimethylamino)phenyl, optical isomers thereof in pure form or in the form of a mixture, and pharmaceutically acceptable addition salts thereof with an acid or base, it being understood that: the terms "alkyl" and "alkoxy" represent straight-chained or branched radicals having from 1 to 6 carbon atoms. The compounds of the invention and the pharmaceutical compositions comprising them are proving to be useful in the treatment of disorders associated with $I_1$-receptors.

12 Claims, No Drawings

5-(ARLOXYMETHYL)OXAZOLINES

The invention relates to new 5-(aryloxymethyl) oxazolines, a process for the preparation thereof and pharmaceutical compositions containing them.

5-[(2,4,6-trihalophenoxy)methyl]-2-oxazolines (U.S. Pat. No. 3,818,028), which are described as anti-depressants, and 5-[(3,4-dihalophenoxy)methyl]-2-oxazolines (U.S. Pat. No. 3,637,726), which are described as anti-microbial agents, are known from the literature.

The publication by C. Jarry et al (*Eur. J. Med. Chem.*, 25(4), (1990), 379–382) presents phenoxymethyloxazolines that are used as starting materials in the synthesis of phenacylimino-oxazolidines.

5-(phenylphenoxymethyl)-2-oxazolines that have antidepressant properties have also been described in patent specification EP-A-392 929.

Finally, C. Jarry et al (*Bull. Soc. Pharm. Bordeaux*, (1981), 120, 153–162) have demonstrated the anti-hypertensive properties of certain 2-amino-2-oxazolines. Those compounds, however, have, in addition, a stimulant action of central origin.

The object of the present invention is to find new compounds that have anti-hypertensive properties and do not have secondary effects of central origin.

Thus, the present invention relates to new 5-(aryloxymethyl)oxazolines having a strong affinity for the imidazoline $I_1$-receptors ($I_1$-receptor).

Surprisingly, that affinity is selective, since the compounds of the invention do not have comparable affinity for the imidazoline $I_2$-receptors ($I_2$-receptors) or for the $\alpha_1$- and $\alpha_2$-adrenoreceptors which are responsible for the secondary effects of central origin.

As a result, the compounds of the invention will advantageously be used therapeutically in the treatment of pathologies associated with $I_1$-receptors, especially in hypertension.

The absence of affinity for the $\alpha$-receptors makes it possible to avoid the undesirable central neuropharmacological effects usually encountered in that type of treatment.

The invention relates to compounds of formula (I):

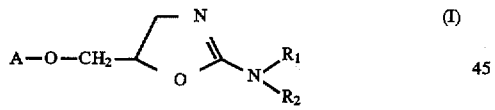
(I)

wherein:

$R_1$ and $R_2$ are selected, each independently of the other, from hydrogen and an alkyl radical, A is selected from the radicals:

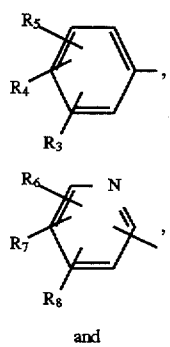

(A₁)

(A₂)

and

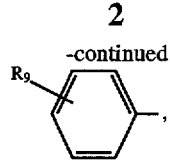
(A₃)

wherein:

$R_3$ represents a radical selected from halogen, alkyl, alkoxy, amino, alkylamino, dialkylamino, carboxy, alkoxycarbonyl, 2-acetyl, trifluoromethyl and cyano, $R_4$, $R_5$, $R_6$, $R_7$ and $R_8$ are selected, each independently of the others, from hydrogen, a halogen, an alkyl, alkoxy, amino, alkylamino, dialkylamino, carboxy, alkoxycarbonyl, cyano and a trifluoromethyl radical, $R_9$ represents the nitro radical, with the proviso that A cannot represent a grouping selected from: dihalophenyl, trihalophenyl, 4-methylphenyl, 4-chlorophenyl, 4-methoxyphenyl, 4-tert-butylphenyl and 3-(dimethylamino)phenyl, optical isomers thereof in pure form or in the form of a mixture, and pharmaceutically acceptable addition salts thereof with an acid or base, it being understood that: the terms "alkyl" and "alkoxy" represent straight-chained or branched radicals having from 1 to 6 carbon atoms.

The invention relates especially to the compounds of formula (I) wherein A represents the radical of formula ($A_1$) as defined in formula (I).

The invention relates especially to the compounds of formula (I) wherein A represents the radical of formula ($A_2$) as defined in formula (I).

The invention relates especially to the compounds of formula (I) wherein A represents the radical of formula ($A_4$):

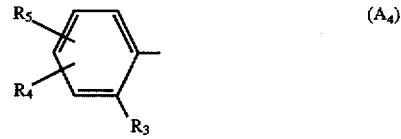
(A₄)

wherein $R_3$, $R_4$ and $R_5$ are as defined in formula (I).

The invention relates more especially to the compounds of formula (I) wherein A represents the radical of formula ($A_6$):

(A₆)

a particular case of the radical ($A_1$) as defined in formula (I) wherein each of $R_4$ and $R_5$ represents hydrogen.

The invention relates, for example, to the compounds of formula (I) wherein A represents a radical of formula $A_6$ and $R_3$ is selected from halogen, alkyl and alkoxy, especially alkyl.

Among the pharmaceutically acceptable acids that may be used to form an addition salt with the compounds of the invention, the following acids may be mentioned, by way of non-limiting example: hydrochloric, sulphuric, phosphoric, tartaric, malic, maleic, fumaric, oxalic, methanesulphonic, ethanesulphonic, camphoric and citric acid.

Among the pharmaceutically acceptable bases that may be used to form an addition salt with the compounds of the invention there may be mentioned, by way of non-limiting example, sodium, potassium, calcium and aluminium hydroxides, alkali metal and alkaline earth metal carbonates, and organic bases, such as triethylamine, benzylamine, diethanolamine, tert-butylamine, dicyclohexylamine and arginine.

More especially, alkyl radicals present in formula (I) are selected from methyl, ethyl, n-propyl, isopropyl, n-butyl, isobutyl, sec-butyl, tert-butyl, pentyl and hexyl.

Alkoxy radicals present in formula (I) are selected from methoxy, ethoxy, n-propoxy, isopropoxy, n-butoxy, isobutoxy, sec-butoxy, tert-butoxy, pentyloxy and hexyloxy.

Halogens present in formula (I) are selected from bromine, chlorine, fluorine and iodine.

The invention relates also to a process for the preparation of the compounds of formula (I), characterised in that a compound of formula (II):

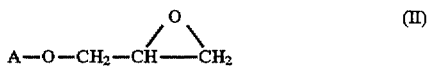

wherein A is as defined in formula (I) is reacted with sodium cyanamide to obtain a compound of formula (I/a):

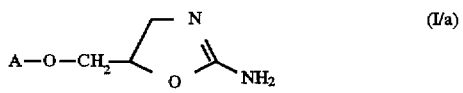

wherein A is as defined hereinbefore, which compound of formula (I/a) is then mono- or di-alkylated at the primary amine to obtain a compound of formula (I/b) corresponding to a compound of formula (I) wherein $R_1$ and/or $R_2$ represent alkyl, the compounds of formulae (I/a) and (I/b) forming the totality of the compounds of formula (I), which compounds of formula (I) may, if desired, be

- purified in accordance with one or more purification methods selected from crystallisation, chromatography on silica gel, extraction, filtration and passing over carbon or resin,
- separated, where appropriate, in pure form or in the form of a mixture, into their possible optical isomers using conventional separation techniques,
- or converted into pharmaceutically acceptable salts with an acid or base.

The starting materials used in the process for the preparation of the compounds of formula (I) are either commercial products or are readily obtainable by a person skilled in the art.

For example, compounds of formula (I) are obtained in a customary manner from phenol or the corresponding pyridinol and epichlorohydrin.

In order to obtain sodium cyanamide, sodium ethanolate is reacted with cyanamide in ethanol.

The compounds of formula (I) have very valuable pharmacological properties from the point of view of the clinician and the doctor.

The compounds of the invention and the pharmaceutical compositions comprising them are proving to be useful in the treatment of disorders associated with $I_1$-receptors.

In fact, $I_1$-receptors are known to be the mediators of a hypotensive action of a central type, as has been demonstrated in studies on the effects of rilmenidine.

$I_1$-receptors are also known to be involved in stimulating the release of insulin by the β cells of the pancreas (Schulz et al., *Naunyn-Schmiedeberg's Arch. Pharmacol.*, (1989), 340 (6),712–714).

$I_1$ receptors are also implicated in anaemia, especially sickle cell anaemia, and in cancerous proliferation.

Now, the pharmacological study of compounds of the invention has demonstrated that they are not toxic and have a very strong selective affinity for $I_1$-receptors.

This allows it to be established that compounds of the invention are useful in the treatment of cardiovascular pathologies and especially hypertension, in particular essential arterial hypertension, and also in the treatment of diabetes, anaemia, especially sickle cell anaemia, and cancer.

The compounds will be used preferably in the treatment of essential arterial hypertension.

The present invention relates also to pharmaceutical compositions comprising the compounds of formula (I) or, where appropriate, a pharmaceutically acceptable addition salt thereof with an acid or base, in combination with one or more pharmaceutically acceptable excipients.

Among the pharmaceutical compositions according to the invention, there may be mentioned more especially those which are suitable for oral, parenteral, nasal, per- or transcutaneous, rectal, perlingual, ocular or respiratory administration and especially tablets or dragées, sublingual tablets, sachets, packets, gelatin capules, glossettes, lozenges, suppositories, creams, ointments, dermal gels and drinkable or injectable ampoules.

The dosage varies according to the sex, age and weight of the patient, the mode of administration, the nature of the therapeutic indication and possibly associated treatments, and ranges from 0.1 mg to 100 mg per 24 hours in 1 or 2 doses, more especially from 1 to 10 mg, for example from 1 to 2 mg.

The following Examples illustrate the invention but do not limit it in any way.

EXAMPLES 1 TO 25

The compounds of the following Examples are obtained by proceeding as described in the general method of operation and using a suitably substituted epoxide:

General Method of Operation

The oxazoline heterocycle is formed by opening up the epoxide ring by the action of sodium cyanamide. That reaction is carried out in methanol, which has the advantage of rendering the medium homogeneous and especially of preventing hydrolysis of the sodium cyanamide. Yields are satisfactory.

0.2 mole of sodium cyanamide and 200 cm³ of anhydrous methanol are introduced into a reactor. Once dissolution is complete, 0.2 mole of epoxide is added dropwise; the temperature is advantageously maintained below +20°. After twelve hours' stirring, 4,5-dihydro-oxazol-2-ylamine sometimes separates out in the solid state. It is purified by fractional crystallisation. When the reaction medium remains homogeneous, the methanol is removed by evaporation. The solid residue is a mixture of 4,5-dihydro-oxazol-2-ylamine and sodium methanolate. Removal of the latter by washing with water gives the same result as in the case above.

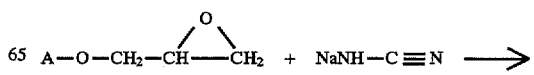

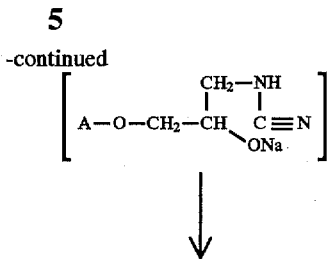

↓

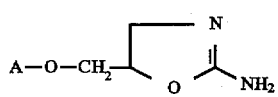

EXAMPLE 1

5-[(2-METHYLPHENOXY)METHYL]-4,5-DIHYDRO-OXAZOL-2-YLAMINE white crystalline powder Melting point (m.p.)=130° C. (heptane) pKa=8.54 log $P_{o/w}$=1.69 dipole moment: benzene: 1.80 D dioxane: 2.07 D IR ($cm^{-1}$) KBr disk: ν (NH): 3410; ν (C≡N): 1680

$^1$H NMR ($CDCl_3$) internal reference TMS, δ (ppm): 7.0 (m, 4H, arom); 4.91 (m, 1H, CH—O); 4.88 (s, 2H, $NH_2$); 3.86 (m, 4H, $CH_2$); 2.3 (s, 3H, $CH_3$)

Elemental analysis: $C_{11}H_{14}N_2O_2$ (M=206)

|  | % C | % H | % N |
|---|---|---|---|
| Calculated: | 64.08 | 6.80 | 13.59 |
| Found: | 64.09 | 6.84 | 13.52 |

Preparation: Epoxide: boiling point (b.p.): 88° C. (53.31 Pa) Yield: 49% Yield (oxazoline): 51%

EXAMPLE 2

5-[(3-METHYLPHENOXY)METHYL]-4,5-DIHYDRO-OXAZOL-2-YLAMINE

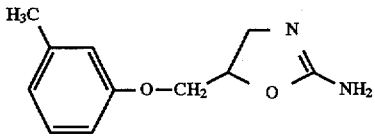

white crystalline powder m.p.=130° C. ($C_2HCl_3$)

IR ($cm^{-1}$) KBr disk: ν (NH): 3420; ν (C≡N): 1685

$^1$H NMR ($CDCl_3$), internal reference TMS, δ (ppm): 7.00 (m, 4H, arom); 4.90 (m, 1H, CH—O); 4.30 (s, 2H, $NH_2$); 3.82 (m, 4H, $CH_2$); 2.34 (s, 3H, $CH_3$)

Elemental analysis: $C_{11}H_{14}N_2O_2$ (M=206)

|  | % C | % H | % N |
|---|---|---|---|
| Calculated: | 64.08 | 6.80 | 13.59 |
| Found: | 64.07 | 6.77 | 13.44 |

Preparation: Epoxide: b.p.: 100° C. (66.64 Pa) Yield: 72% Yield (oxazoline): 43%

EXAMPLE 3

5-[(2-CHLOROPHENOXY)METHYL]-4,5-DIHYDRO-OXAZOL-2-YLAMINE $C_{10}H_{11}N_2O_2Cl$ (M=226.45) m.p.=142° C. ($C_2HCl_3$) Yield: 21%

EXAMPLE 4

5-[(3-CHLOROPHENOXY)METHYL]-4,5-DIHYDRO-OXAZOL-2-YLAMINE $C_{10}H_{11}N_2O_2Cl$ (M=226.45) m.p.=128° C. ($CCl_4$) Yield: 24%

EXAMPLE 5

5-[(2-METHOXYPHENOXY)METHYL]-4,5-DIHYDRO-OXAZOL-2-YLAMINE $C_{11}H_{14}N_2O_3$ (M=222) m.p.=110° C. ($C_2HCl_3$) Yield: 13%

EXAMPLE 6

5-[(3-METHOXYPHENOXY)METHYL]-4,5-DIHYDRO-OXAZOL-2-YLAMINE $C_{11}H_{14}N_2O_3$ (M=222) m.p.=110° C. Yield: 28%

EXAMPLE 7

5-[(2-ETHOXYPHENOXY)METHYL]-4,5-DIHYDRO-OXAZOL-2-YLAMINE $C_{12}H_{16}N_2O_3$ (M=236) m.p.=130° C. ($CCl_4$) Yield: 21%

EXAMPLE 8

5-[(4-ETHYLPHENOXY)METHYL]-4,5-DIHYDRO-OXAZOL-2-YLAMINE $C_{12}H_{16}N_2O_2$ (M=220) m.p.=172° C. ($C_2H_5OH$) Yield: 45%

EXAMPLE 9

5-[(2,6-DIMETHYLPHENOXY)METHYL]-4,5-DIHYDRO-OXAZOL-2-YLAMINE $C_{12}H_{16}N_2O_2$ (M=220) m.p.=114° C. (heptane) Yield: 24%

EXAMPLE 10

5-[(2,4-DIMETHYLPHENOXY)METHYL]-4,5-DIHYDRO-OXAZOL-2-YLAMINE $C_{12}H_{16}N_2O_2$ (M=220) m.p.=116° C. (heptane) Yield: 31%

EXAMPLE 11

5-[(3,4-DIMETHYLPHENOXY)METHYL]-4,5-DIHYDRO-OXAZOL-2-YLAMINE $C_{12}H_{16}N_2O_2$ (M=220) m.p.=144° C. ($C_2HCl_3$) Yield: 21%

EXAMPLE 12

5-{[4-(1,1-DIMETHYLPROPYL)PHENOXY]METHYL}-4,5-DIHYDRO-OXAZOL-2-YLAMINE $C_{15}H_{22}N_2O_2$ (M=262) m.p.=104° C. (heptane) Yield: 11%

EXAMPLE 13

5-[(2,3-DIMETHYLPHENOXY)METHYL]-4,5-DIHYDRO-OXAZOL-2-YLAMINE m.p.=175° C. ($C_2H_5OH$)

EXAMPLE 14

5-[(3-NITROPHENOXY)METHYL]-4,5-DIHYDRO-OXAZOL-2-YLAMINE

EXAMPLE 15

5-[(4-NITROPHENOXY)METHYL]-4,5-DIHYDRO-OXAZOL-2-YLAMINE

EXAMPLE 16

5-[(2,5-DIMETHYLPHENOXY)METHYL]-4,5-DIHYDRO-OXAZOL-2-YLAMINE m.p.=131° C. ($C_2HCl_3$)

EXAMPLE 17

5-[(4-CHLORO-2-METHYLPHENOXY)METHYL]-4,5-DIHYDRO-OXAZOL-2-YLAMINE m.p.=130° C. ($C_2Cl_4$)

EXAMPLE 18

5-[(2-ETHYLPHENOXY)METHYL]-4,5-DIHYDRO-OXAZOL-2-YLAMINE m.p.=109° C. ($C_2Cl_4$)

EXAMPLE 19

5-[(2-ISOPROPYLPHENOXY)METHYL]-4,5-DIHYDRO-OXAZOL-2-YLAMINE m.p.=134° C. ($C_2Cl_4$)

EXAMPLE 20

5-[(2-FLUOROPHENOXY)METHYL]-4,5-DIHYDRO-OXAZOL-2-YLAMINE m.p.=124° C. ($CHCl_3$)

EXAMPLE 21

5-[(2-NITROPHENOXY)METHYL]-4,5-DIHYDRO-OXAZOL-2-YLAMINE m.p.=166° C. (toluene)

EXAMPLE 22

5-[(2-CYANOPHENOXY)METHYL]-4,5-DIHYDRO-OXAZOL-2-YLAMINE m.p.=146° C. (toluene)

EXAMPLE 23

5-[(2-ACETYLPHENOXY)METHYL]-4,5-DIHYDRO-OXAZOL-2-YLAMINE m.p.=142° C. ($C_2Cl_4$)

EXAMPLE 24

5-[(3-TRIFLUOROMETHYLPHENOXY)METHYL]-4,5-DIHYDRO-OXAZOL-2-YLAMINE m.p.=10° C. (heptane)

EXAMPLE 25

5-[(2,6-DIMETHOXYMETHYLPHENOXY)METHYL]-4,5-DIHYDRO-OXAZOL-2-YLAMINE m.p.=180° C. ($C_2HCl_3$)

EXAMPLE 26

N-n-PROPYL-N-[5-(2-METHYLPHENOXY)METHYL-4,5-DIHYDRO-OXAZOL-2-YL]AMINE

In a reactor are introduced 0,01 mol of 5-[(2-methylphenoxy)methyl]-4,5-dihydro-oxazol-2-ylamine and 100 ml of acetone. Once dissolution is complete, 0,005 mol of 1-bromopropyl are added and the whole is heated to ebullition during 48 hours. After filtering off the formed solid and evaporating the solvent, the crude desired product is purified by separation by column chromatography (eluent: chloroform/ammonia, 95:5).

$C_{14}H_{20}N_2O_2$ M=248 White crystalline powder m.p.=108° C. (heptane)

EXAMPLE 27

N-ETHYL-N-[5-(2-METHYLPHENOXY)METHYL-4,5-DIHYDRO-OXAZOL-2-YL]AMINE

By proceeding in a manner analogous to that described in Example 26, replacing 1-bromopropyl by 1-bromoethyl, the title compound is obtained.

F=126° C. (heptane)

EXAMPLE 28

5-[(2-METHYLPHENOXY)METHYL]-4,5-DIHYDRO-OXAZOL-2-YLAMINE (Isomer 1 of the compound of Example 1).

That isomer was obtained from the compound of Example 1 (racemic) by separation by chromatography under the following conditions:

Column: CHIRALCEL OD Eluant: n-heptane/ethanol/diethylamine: 900/100/0.4 Rate of flow: 1 ml/min. Injection: 4 μl of a solution of 4 mg/ml (dichloromethane/isopropanol mixture: 50/50) Detection: 220 nm.

EXAMPLE 29

5-[(2-METHYLPHENOXY)METHYL]-4,5-DIHYDRO-OXAZOL-2-YLAMINE (Isomer 2 of the compound of Example 1)

Enantiomer of the compound described in Example 28, obtained according to the same process, starting from the compound of Example 1 (racemic).

PHARMACOLOGICAL STUDY

EXAMPLE A: PROFILE OF BINDING TO IMIDAZOLINE $I_1$- AND $I_2$-RECEPTORS. (IN VITRO STUDY)

OBJECT:

To measure in vitro the binding affinity of the compounds of the invention for $I_1$- and $I_2$-receptors, by determining the capacity of those compounds to displace specific radioligands of the imidazoline $I_1$- and $I_2$-receptors.

PROTOCOL:

The following Table gives the radioligand used to label the receptor, the compound and the concentration selected to determine the non-specific fraction and the tissue selected.

| Receptor or site | Radioligand | non specific | Structure |
|---|---|---|---|
| $I_1$ | [3H]-clonidine + 10 μM of norepinephrine | $10^{-5}$ M cold clonidine | bovine lateral reticular nucleus |
| $I_2$ | [3H]-idazoxane + 10 μM of norepinephrine | $10^{-5}$ M idazoxane | rabbit renal cortex |

RESULTS:

The results obtained in vitro on the central or peripheral receptors and under our experimental conditions demonstrate that the compounds of the invention have a very strong affinity for the $I_1$ sites (see Table 1), whilst they bind with only very weak affinity to the $I_2$-receptors of rabbit renal cortex.

TABLE 1

Profile of binding to the $I_1$ - and $I_2$ -receptors

| | $K_i(M)$ | |
|---|---|---|
| EXAMPLE | $I_1$ | $I_2$ |
| 1 | $8.5 \times 10^{-9}$ | $9.2 \times 10^{-7}$ |
| 9 | $5.7 \times 10^{-8}$ | $2.1 \times 10^{-6}$ |
| 10 | $1.6 \times 10^{-7}$ | $3.9 \times 10^{-6}$ |
| 13 | $6.4 \times 10^{-8}$ | $4.5 \times 10^{-7}$ |
| 16 | $8.5 \times 10^{-8}$ | $1.6 \times 10^{-6}$ |
| 17 | $1.2 \times 10^{-7}$ | $1.0 \times 10^{-6}$ |
| 18 | $1.0 \times 10^{-7}$ | $1.8 \times 10^{-6}$ |
| 19 | $1.2 \times 10^{-7}$ | $2.1 \times 10^{-6}$ |
| 20 | $2.1 \times 10^{-7}$ | $1.3 \times 10^{-6}$ |
| 21 | $5.0 \times 10^{-7}$ | $3.9 \times 10^{-6}$ |
| 22 | $4.8 \times 10^{-8}$ | $2.4 \times 10^{-6}$ |
| 23 | $1.7 \times 10^{-7}$ | $7.7 \times 10^{-6}$ |
| 26 | $6.7 \times 10^{-7}$ | $1.4 \times 10^{-6}$ |
| 27 | $1.7 \times 10^{-7}$ | $1.0 \times 10^{-6}$ |
| 28 | $3.7 \times 10^{-7}$ | $1.3 \times 10^{-5}$ |
| 29 | $5.8 \times 10^{-9}$ | $7.5 \times 10^{-6}$ |

EXAMPLE B: PROFILE OF BINDING TO THE CENTRAL ALPHA 1- AND ALPHA 2-ADRENORECEPTORS. (IN VITRO STUDY)

OBJECT:

To measure in vitro the binding affinity of the compounds of the invention for the central alpha 1- ($\alpha_1$-) and alpha 2- ($\alpha_2$-) receptors by determining the capacity of the compound in question to displace specific radioligands of those receptors.

RESULTS:

The results obtained in vitro on the adrenoreceptors under our experimental conditions demonstrate that the compounds of the invention have only very weak affinity for the alpha 1-adrenoreceptors ($K_i>7$ μM) and for the alpha 2-adrenoreceptors ($K_i>10$ μM).

PROTOCOL:

The following Table gives the radioligand used to label the receptor, the compound and the concentration selected to determine the non-specific fraction and the tissue selected.

| Receptor or site | Radioligand | non specific | Structure |
|---|---|---|---|
| Alpha 1 | [3H]-prazosin | $10^{-5}$ M phentolamine | calf frontal cortex |

-continued

| Receptor or site | Radioligand | non specific | Structure |
|---|---|---|---|
| Alpha 2 | [3H]-RX 821002 | $10^{-5}$ M yohimbine | calf frontal cortex |

EXAMPLE C: PHARMACEUTICAL COMPOSITION: TABLETS

Tablets each containing 1 mg of 5-[(2-methylphenoxy)methyl]-4,5-dihydro-oxazol-2-ylamine

| | |
|---|---|
| 5-[(2-methylphenoxy)methyl]-4,5-dihydro-oxazol-2-ylamine | 1 g |
| Wheat starch | 20 g |
| Corn starch | 20 g |
| Lactose | 30 g |
| Magnesium stearate | 2 g |
| Silica | 1 g |
| Hydroxypropy cellulose | 2 g |

We claim:

1. A compound selected from those of formula (I):

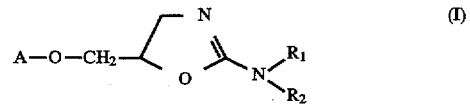

wherein:

R$_1$ and R$_2$ are selected, each independently of the other, from hydrogen and alkyl, A is selected from the radicals:

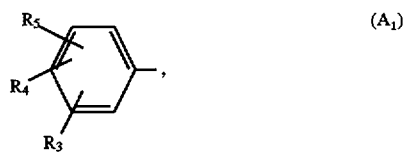

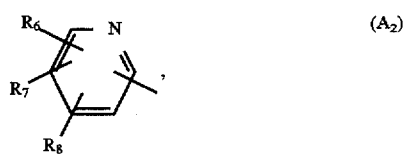

and

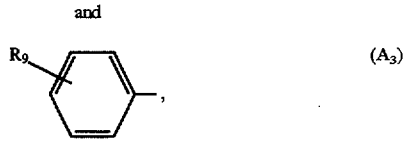

wherein:

R$_3$ represents a radical selected from halogen, alkyl, alkoxy, amino, alkylamino, dialkylamino, carboxy, alkoxycarbonyl, 2-acetyl, trifluoromethyl, and cyano, R$_4$, R$_5$, R$_6$, R$_7$ and R$_8$ are selected, each independently of the others, from hydrogen, halogen, alkyl, alkoxy, amino, alkylamino, dialkylamino, carboxy, alkoxycarbonyl, cyano, and trifluoromethyl, R$_9$ represents nitro, with the proviso that A cannot represent a grouping selected from: dihalophenyl, trihalophenyl, 4-methylphenyl, 4-chlorophenyl, 4-methoxyphenyl, 4-tert-butylphenyl, and 3-(dimethylamino)phenyl, optical isomers thereof, and pharmaceutically-acceptable addition salts thereof with an acid or base, it being understood that: the terms "alkyl" and "alkoxy" represent straight-chained or branched radicals having 1 to 6 carbon atoms inclusive.

2. A compound selected from those of formula (I), wherein A represents the radical of formula (A₄):

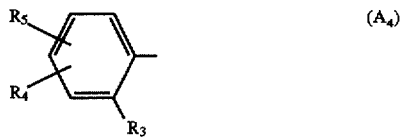

wherein R₃, R₄ and R₅ are as defined in formula (I).

3. A compound selected from those of formula (I) according to claim 1, wherein A represents the radical of formula (A₆):

wherein R₃ is as defined in claim 1.

4. A compound according to claim 1 which is 5-[(2-methylphenoxy)methyl]-4,5-dihydro-oxazol-2-ylamine.

5. A compound according to claim 1 which is (5R*)-5-[(2-methylphenoxy)methyl]-4,5-dihydro-oxazol-2-ylamine.

6. A compound according to claim 1 which is 5-[(2,5-dimethylphenoxy)methyl]-4,5-dihydro-oxazol-2-ylamine.

7. A compound according to claim 1 which is 5-[2,6-(dimethyl)phenoxymethyl]-2-amino-2-oxazoline.

8. A compound according to claim 1 which is N-n-propyl-N-[5-(2-methylphenoxy)methyl-4,5-dihydro-oxazol-2-yl]amine.

9. A compound according to claim 1 which is N-ethyl-N-[5-(2-methylphenoxy)methyl-4,5-dihydro-oxazol-2-yl]amine.

10. A method for treating a mammal afflicted with a disease requiring a selective $I_1$-receptor ligand comprising the step of administering to said mammal an amount of a compound of claim 1 which is effective for alleviation of said disease.

11. A pharmaceutical composition useful as a selective $I_1$-receptor ligand comprising an amount of a compound as claimed in claim 1 which is effective as a selective $I_1$-receptor ligand, together with a pharmaceutically-acceptable excipient.

12. A method of claim 10 wherein the compound is in the form of a pharmaceutical composition together with a pharmaceutically acceptable excipient.

* * * * *

UNITED STATES PATENT AND TRADEMARK OFFICE
CERTIFICATE OF CORRECTION

PATENT NO. : 5,686,477
DATED : Nov. 11, 1997
INVENTOR(S) : C. Jarry; I. Forfar; J.J. Bose; P. Renard; E. Scalbert; B. Guardiola It is certified that error appears in the above-indentified patent and that said Letters Patent is hereby corrected as shown below:

Title Page, [54]: Title should read
-- 5-(ARYLOXYMETHYL)OXAZOLINES --.

Column 1, line 1: Title should read
-- 5-(ARYLOXYMETHYL)OXAZOLINES --.

Signed and Sealed this

Third Day of February, 1998

Attest:

BRUCE LEHMAN

Attesting Officer

Commissioner of Patents and Trademarks